(12) United States Patent
Stuelpnagel et al.

(10) Patent No.: US 7,604,996 B1
(45) Date of Patent: Oct. 20, 2009

(54) COMPOSITIONS AND METHODS FOR PREPARING OLIGONUCLEOTIDE SOLUTIONS

(75) Inventors: John R. Stuelpnagel, Encinitas, CA (US); Mark S. Chee, Del Mar, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 09/642,068

(22) Filed: Aug. 18, 2000

Related U.S. Application Data

(60) Provisional application No. 60/149,344, filed on Aug. 18, 1999.

(51) Int. Cl.
*C12Q 1/68* (2006.01)
*C12P 19/34* (2006.01)
*C12M 1/34* (2006.01)
*C12M 3/00* (2006.01)
*C07H 21/02* (2006.01)
*C07H 21/04* (2006.01)

(52) U.S. Cl. ................ 436/6; 435/91.2; 435/287.1; 536/23.1; 536/24.3; 977/792

(58) Field of Classification Search ............ 435/6
See application file for complete search history.

(56) References Cited

U.S. PATENT DOCUMENTS

| | | | |
|---|---|---|---|
| 4,200,110 A | 4/1980 | Peterson et al. | |
| 4,499,052 A | 2/1985 | Fulwyler | |
| 4,682,895 A | 7/1987 | Costello | |
| 4,785,814 A | 11/1988 | Kane | |
| 4,822,746 A | 4/1989 | Walt | |
| 4,824,789 A | 4/1989 | Yafuso et al. | |
| 4,999,306 A | 3/1991 | Yafuso et al. | |
| 5,002,867 A | 3/1991 | Macevicz | |
| 5,028,545 A | 7/1991 | Soini | |
| 5,105,305 A | 4/1992 | Betzig et al. | |
| 5,114,864 A | 5/1992 | Walt | |
| 5,132,242 A | 7/1992 | Cheung | |
| 5,143,853 A | 9/1992 | Walt | |
| 5,194,300 A | 3/1993 | Cheung | |
| 5,244,636 A | 9/1993 | Walt et al. | |
| 5,244,813 A | 9/1993 | Walt et al. | |
| 5,250,264 A | 10/1993 | Walt et al. | |
| 5,252,494 A | 10/1993 | Walt | |
| 5,254,477 A | 10/1993 | Walt | |
| 5,298,741 A | 3/1994 | Walt et al. | |
| 5,302,509 A | 4/1994 | Cheeseman | |
| 5,320,814 A | 6/1994 | Walt et al. | |
| 5,357,590 A | 10/1994 | Auracher | |
| 5,380,489 A | 1/1995 | Sutton et al. | |
| 5,435,724 A | 7/1995 | Goodman et al. | |
| 5,445,934 A | 8/1995 | Fodor | |
| 5,474,895 A | 12/1995 | Ishii et al. | |
| 5,481,629 A | 1/1996 | Tabuchi | |
| 5,494,798 A | 2/1996 | Gerdt et al. | |
| 5,494,810 A | 2/1996 | Barany et al. | |
| 5,496,997 A | 3/1996 | Pope | |
| 5,512,490 A | 4/1996 | Walt et al. | |
| 5,516,635 A | 5/1996 | Ekins et al. | |
| 5,518,883 A | 5/1996 | Soini | |
| 5,565,324 A | 10/1996 | Still et al. | |
| 5,573,909 A | 11/1996 | Singer et al. | |
| 5,575,849 A | 11/1996 | Honda et al. | |
| 5,604,097 A | 2/1997 | Brenner | |
| 5,633,972 A | 5/1997 | Walt et al. | |
| 5,639,603 A | 6/1997 | Dower et al. | |
| 5,650,489 A * | 7/1997 | Lam et al. | .................... 530/334 |
| 5,656,241 A | 8/1997 | Seifert et al. | |
| 5,679,524 A | 10/1997 | Nikiforov et al. | |
| 5,679,773 A * | 10/1997 | Holmes | .................... 530/344 |
| 5,690,894 A | 11/1997 | Pinkel et al. | |
| 5,763,175 A | 6/1998 | Brenner | |
| 5,780,231 A | 7/1998 | Brenner | |
| 5,795,714 A | 8/1998 | Cantor et al. | |
| 5,814,524 A | 9/1998 | Walt | |
| 5,830,711 A | 11/1998 | Barany et al. | |
| 5,840,256 A | 11/1998 | Demers et al. | |
| 5,843,655 A | 12/1998 | McGall | |
| 5,854,684 A | 12/1998 | Stabile et al. | |
| 5,856,083 A | 1/1999 | Chelsky et al. | |

(Continued)

FOREIGN PATENT DOCUMENTS

EP 0 269 764 6/1988

(Continued)

OTHER PUBLICATIONS

Lashkari, D. A. et al., "An automated multiplex oligonucleotide synthesizer: Development of high-throughput, low-cost DNA synthesis", PNAS USA, vol. 92, pp. 7912-7915 (1995).*

(Continued)

*Primary Examiner*—Teresa E Strzelecka
(74) *Attorney, Agent, or Firm*—McDermott Will & Emery LLP

(57) ABSTRACT

The present invention is directed to methods and compositions for generating a pool of oligonucleotides. The invention finds use in preparing a population or subpopulations of oligonucleotides in solution. The pool of oligonucleotides finds use in a variety of nucleic acid detection and/or amplification assays.

22 Claims, 3 Drawing Sheets

U.S. PATENT DOCUMENTS

| | | | |
|---|---|---|---|
| 5,858,732 | A | 1/1999 | Solomon et al. |
| 5,863,708 | A | 1/1999 | Zanzucchi et al. |
| 5,888,723 | A | 3/1999 | Sutton et al. |
| 5,900,481 | A | 5/1999 | Lough et al. |
| 6,013,440 | A * | 1/2000 | Lipshutz et al. ............... 435/6 |
| 6,013,456 | A | 1/2000 | Akhavan-Tafti |
| 6,023,540 | A | 2/2000 | Walt et al. |
| 6,027,889 | A | 2/2000 | Barany et al. |
| 6,051,380 | A | 4/2000 | Sosnowski et al. |
| 6,054,564 | A | 4/2000 | Barany et al. |
| 6,083,763 | A | 7/2000 | Balch |
| 6,090,553 | A | 7/2000 | Matson |
| 6,110,678 | A | 8/2000 | Weisburg et al. |
| 6,156,502 | A * | 12/2000 | Beattie .......................... 435/6 |
| 6,172,218 | B1 | 1/2001 | Brenner |
| 6,251,639 | B1 | 6/2001 | Kurn |
| 6,268,147 | B1 * | 7/2001 | Beattie et al. ................. 435/6 |
| 6,268,148 | B1 | 7/2001 | Barany et al. |
| 6,327,410 | B1 * | 12/2001 | Walt et al. ................... 385/115 |
| 6,537,749 | B2 * | 3/2003 | Kuimelis et al. .............. 435/6 |
| 6,586,211 | B1 | 7/2003 | Staehler et al. |
| 7,026,114 | B1 | 4/2006 | Barone et al. |

FOREIGN PATENT DOCUMENTS

| | | |
|---|---|---|
| EP | 0 392 546 | 10/1990 |
| EP | 0 478 319 | 4/1992 |
| EP | 0 723 146 | 7/1996 |
| WO | 89/11101 | 11/1989 |
| WO | WO 92/09300 | 6/1992 |
| WO | 93/02360 | 2/1993 |
| WO | WO 93/25563 A1 | 12/1993 |
| WO | WO 94/02515 | 2/1994 |
| WO | WO 95/16918 | 6/1995 |
| WO | WO 95/33070 | 12/1995 |
| WO | 96/03212 | 2/1996 |
| WO | WO 96/40901 | 12/1996 |
| WO | 97/14028 | 4/1997 |
| WO | 97/14928 | 4/1997 |
| WO | WO 97/31256 A2 | 8/1997 |
| WO | 97/40385 | 10/1997 |
| WO | WO 97/46704 A1 | 12/1997 |
| WO | WO 98/13523 A1 | 4/1998 |
| WO | WO 98/31836 A1 | 7/1998 |
| WO | 98/40726 | 9/1998 |
| WO | 98/50782 | 11/1998 |
| WO | 98/53093 | 11/1998 |
| WO | 98/53300 | 11/1998 |
| WO | 99/18434 | 4/1999 |
| WO | WO 99/39001 | 8/1999 |
| WO | WO 96/30392 A1 | 10/1999 |
| WO | WO 99/53087 | 10/1999 |
| WO | 99/60170 | 11/1999 |
| WO | 99/67414 | 12/1999 |
| WO | WO 99/64867 A1 | 12/1999 |
| WO | WO 99/67641 A2 | 12/1999 |
| WO | WO 00/04372 | 1/2000 |
| WO | WO 00/13004 | 3/2000 |
| WO | WO 00/16101 | 3/2000 |
| WO | WO 00/26411 | 5/2000 |
| WO | WO 00/34299 | 6/2000 |
| WO | WO 00/39587 A1 | 7/2000 |
| WO | WO 00/47996 A2 | 8/2000 |
| WO | WO 00/48000 A1 | 9/2000 |
| WO | WO 00/58516 A2 | 10/2000 |
| WO | WO 00/63437 A2 | 10/2000 |
| WO | WO 00/71243 A1 | 11/2000 |
| WO | WO 00/71995 A2 | 11/2000 |
| WO | WO 99/71992 A1 | 11/2000 |
| WO | WO 00/75373 A2 | 12/2000 |

OTHER PUBLICATIONS

Sinha et al. Nucl. Acids Res., vol. 12, pp. 4539-4557 (1984).*
Nelson et al., Nucl. Acids res., vol. 20, pp. 6253-6259 (1992).*
Pastinen T. et al., Genome Res., vol. 7, pp. 606-614 (1997).*
Weiler, J. et al., Anal. Biochem., vol. 243, pp. 218-227 (1996).*
Shuber, A.P. et al., Genome Res., vol. 5, pp. 488-493 (1995).*
Wang, D.G. et al., Science, vol. 280, pp. 1077-1082 (May 1998).*
Michael, K.L. et al., Anal. Chem., vol. 70, pp. 1242-1248 (1998).*
Ferguson et al., "A Fiber-Optic DNA Biosensor Microarray for the Analysis of Gene Expression," Nature Biotechnology, 14:1681-1684 (1996).
Healey et al., "Improved Fiber-Optic Chemical Sensor for Penicillin," Anal. Chem. 67(24):4471-4476 (1995).
Healey et al., "Development of a Penicillin Biosensor Using a Single Optical Imaging Fiber," SPIE Proc. 2388:568-573 (1995).
Michael et al., "Making Sensors out of Disarray: Optical Sensor Microarrays," Proc. SPIE, 3270: 34-41 (1998).
Michael et al., "Randomly Ordered Addressable High-Density Optical Sensor Arrays," Anal. Chem. 70(7): 1242-1248 (Apr. 1998).
Michael et al., "Fabrication of Micro- and Nanostructures Using Optical Imaging Fibers and there Use as Chemical Sensors," Proc. 3rd Intl. Symp., Microstructures and Microfabricated Systems, ed: P.J. Hesketh, et al., v. 97-5, Electrochem. Soc., 152-157 (Aug. 1997).
Pantano et al., "Ordered Nanowell Arrays," Chem. Mater., 8(12): 2832-2835 (1996).
Walt, "Fiber-Optic Sensors for Continuous Clinical Monitoring," Proc. IEEE, 80(6): 903-911 (1992).
Anonymous, "Fluorescent Microspheres," Tech. Note 19, Bangs Laboratories, (Fishers, In) Feb. 1997.
Anonymous, "Microsphere Selection Guide," Bangs Laboratories, (Fisher, In) Sep. 1998.
Bangs, L.B., "Immunological Applications of Microspheres," The Latex Course, Bangs Laboratories (Carmel, IN) Apr. 1996.
Peterson, J. et al., "Fiber Optic pH Probe for Physiological Use," Anal. Chem., 52:864-869 (1980).
Pope, E. "Fiber Optic Chemical Microsensors Employing Optically Active Silica Microspehres," SPIE, 2388:245-256 (1995).
Strachan et al., "A Rapid General Method for the Identification of PCR Products Using a Fibre-Optic Biosensor and its Application to the Detection of Listeria," Letters in Applied Microbiology, 21:5-9 (1995).
Abel et al., "Fiber-Optic Evanescent Wave Biosensor for the Detection of Oligonucleotides," Anal. Chem. 68:2905-2912 (1996).
Piunno et al., "Fiber-Optic DNA Sensor for Fluorometric Nucleic Acid Determination," Anal. Chem., 67:2635-2643 (1995).
Drmanac, R. et al., "Sequencing by Oligonucleotide Hybridization: A Promising Framework in Decoding of the Genome Program," The First International Conference on Electrophoresis, Supercomputing and the Human Genome, Proceeding of the Apr. 10-13, 1990 Conference at Florida State University. Ed. C. Cantor and H. Lim.
Drmanac, R. et al., "Prospects for a Miniaturized, Simplified and Frugal Human Genome Project," Scientia Yugoslavica, 16(1-2):97-107 (1990).
Drmanac, R. et al., "Sequencing by Hybridization (SBH) with Oligonucleotide Probes as an Integral Approach for the Analysis of Complex Genomes," International Journal of Genome Research, 1(1):59-79(1992).
Drmanac, R. et al., "Sequencing by Hybridization," Automated DNA Sequencing and Analysis, ed. M. Adams, C. Fields and J. Venter. (1994).
Barnard et al.,-"A Fibre-Optic Chemical Sensor with Discrete Sensing Sites," Nature, 353:338-340 (Sep. 1991).
Fuh et al., "Single Fibre Optic Fluorescence pH Probe," Analyst, 112:1159-1163 (1987).
Magnani et al., "In-Vivo Biomedical Monitoring by Fiber-Optic Systems," Journal of Lightwave Technology, 13(7):1396-1406 (1995).
Healey et al., "Fiberoptic DNA Sensor Array Capable of Detecting Point Mutations," Analytical Biochemistry, 251:270-279 (1997).

Hirschfeld et al., "Laser-Fiber-Optic 'Optrode' for Real Time In Vivo Blood Carbon Dioxide Level Monitoring," Journal of Lightwave Technology, LT-5(7):1027-1033 (1987).

Peterson et al., "Fiber-Optic Sensors for Biomedical Applications," Science, 13:123-127 (1984).

Czarnik, "Illuminating the SNP genomic code," Modern Drug Discovery, 1(2):49-55 (1998).

Walt, "Fiber Optic Imaging Sensors", Acc. Chem. Res. 31(5):267-278 (1998).

Lyamichev et al., "Polymorphism identification and quantitative detection of genomic DNA by invasive cleavage of oligonucleotide probes," Nature Biotechnology, 17:292-296 (1999).

Shoemaker et al., "Quantitative phenotypic analysis of yeast deletion mutants using a highly parallel molecular bar-coding strategy," Nature Genetics, 14:450-456 (1996). (A, AS, NA) added Aug. 1, 2001.

Ronaghi et al., "A Sequencing Method Based on Real-Time Pyrophosphate," Science, 281:363-365 (1998).

* cited by examiner

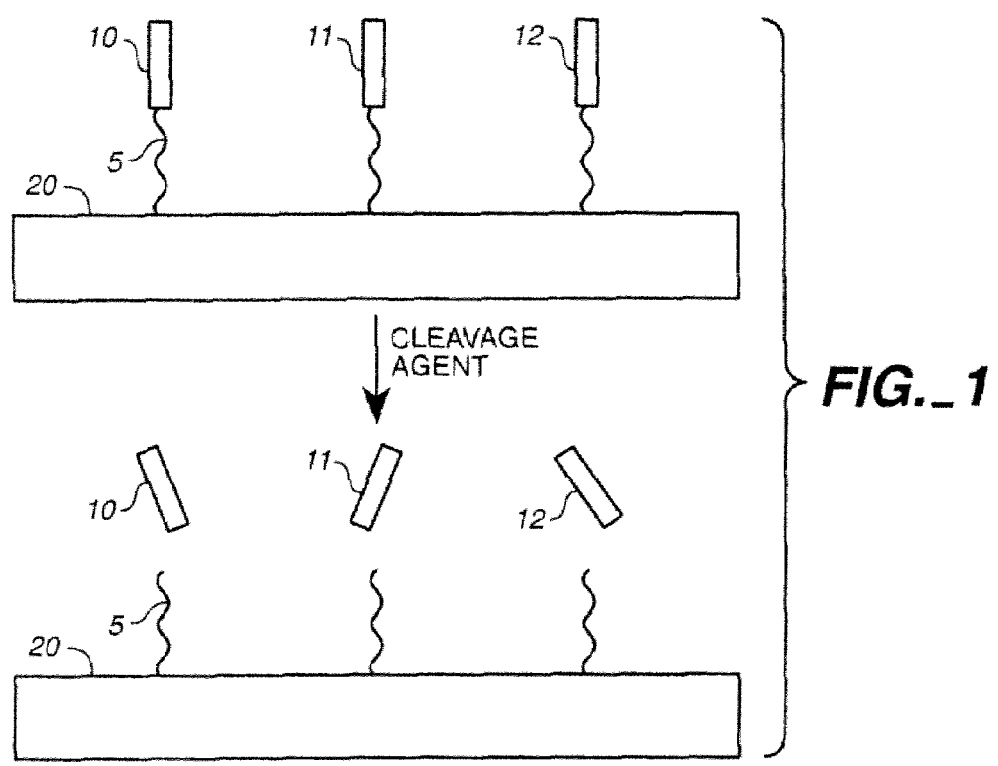
FIG._1

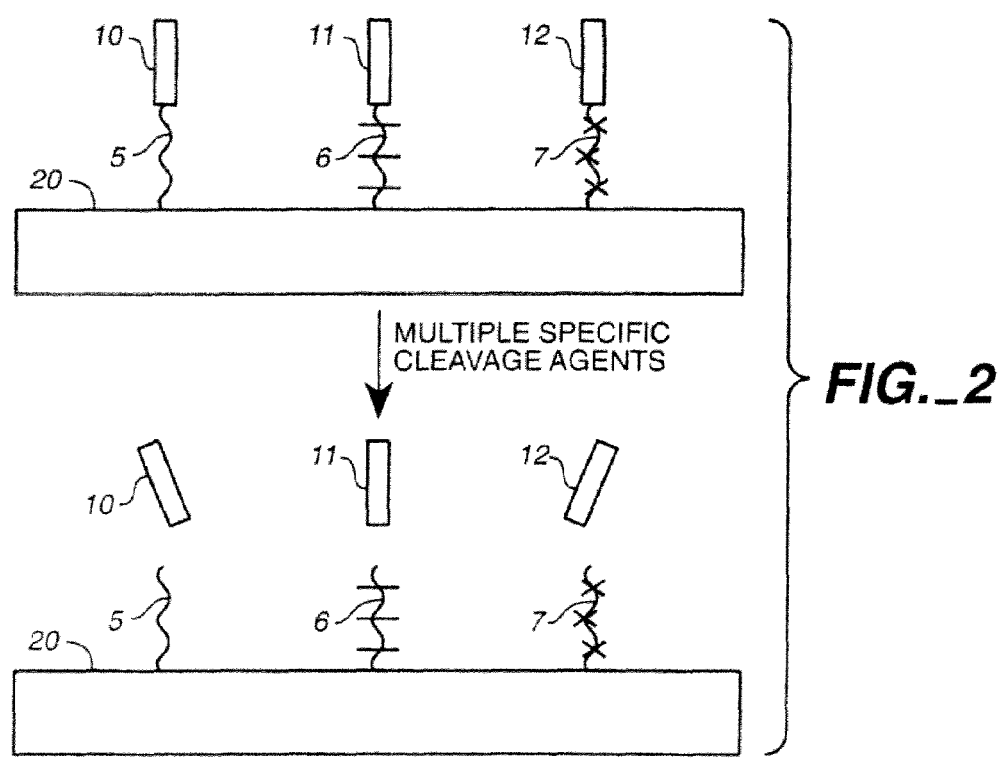
FIG._2

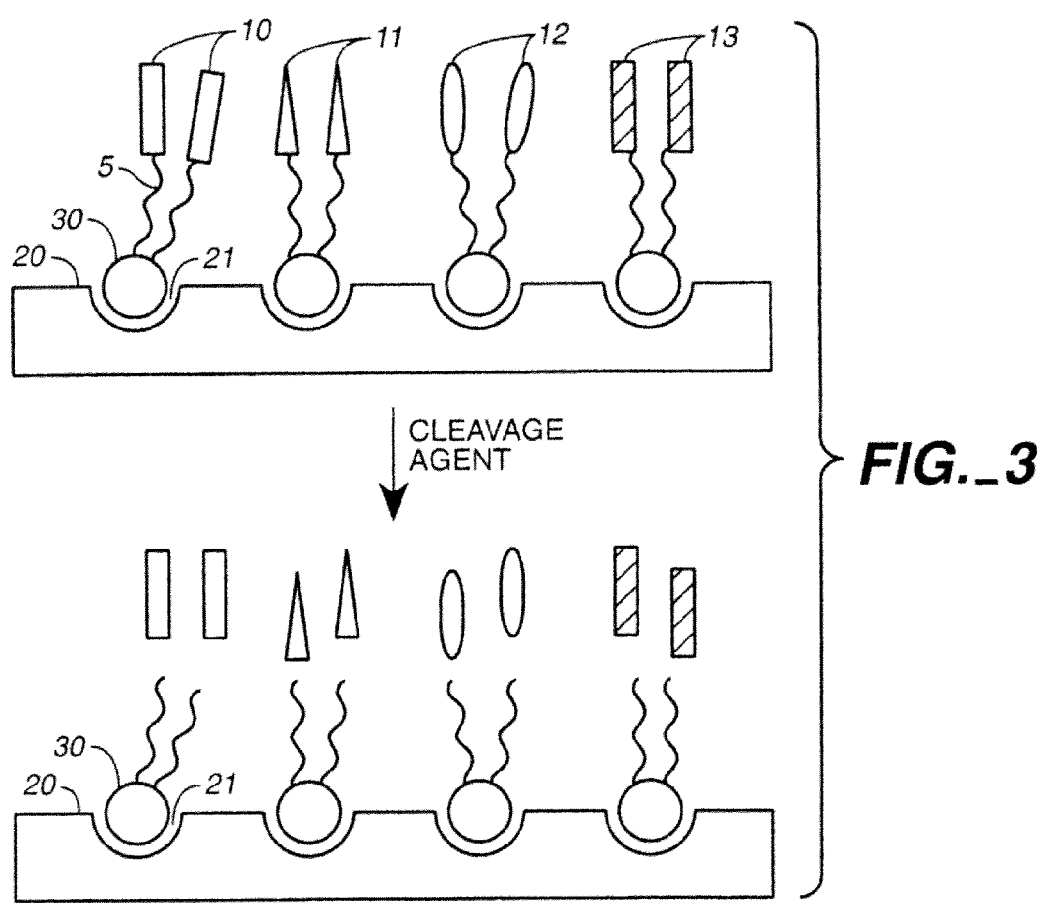
FIG._3

COMPOSITIONS AND METHODS FOR PREPARING OLIGONUCLEOTIDE SOLUTIONS

This application claims the benefit of priority of U.S. provisional application Ser. No. 60/149,344 filed on Aug. 18, 1999.

FIELD OF THE INVENTION

The present invention is directed to methods and compositions for generating a pool of oligonucleotides. The invention finds use in preparing a pool of oligonucleotides in solution. The pool of oligonucleotides finds use in a variety of nucleic acid detection and/or amplification assays.

BACKGROUND OF THE INVENTION

The detection of specific nucleic acids is an important tool for diagnostic medicine and molecular biology research. Gene probe assays currently play roles in identifying infectious organisms such as bacteria and viruses, in probing the expression of normal and mutant genes and identifying mutant genes such as oncogenes, in typing tissue for compatibility preceding tissue transplantation, in matching tissue or blood samples for forensic medicine, and for exploring homology among genes from different species.

A variety of techniques for the detection of nucleic acids have been developed and include techniques that can be classified as either target amplification or signal amplification. Target amplification strategies include the polymerase chain reaction (PCR), strand displacement amplification (SDA), and nucleic acid sequence based amplification (NASBA).

Alternatively, rather than amplify the target, alternate techniques use the target as a template to replicate a signaling probe, allowing a small number of target molecules to result in a large number of signaling probes, that then can be detected. Signal amplification strategies include the ligase chain reaction (LCR), cycling probe technology (CPT), invasive cleavage techniques such as Invader™ technology, Q-Beta replicase (QβR) technology, and the use of "amplification probes" such as "branched DNA" that result in multiple label probes binding to a single target sequence.

The polymerase chain reaction (PCR) is widely used and described, and involves the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference. In addition, there are a number of variations of PCR which also find use in the invention, including "quantitative competitive PCR" or "QC-PCR", "arbitrarily primed PCR" or "AP-PCR", "immuno-PCR", "Alu-PCR", "PCR single strand conformational polymorphism" or "PCR-SSCP", allelic PCR (see Newton et al. Nucl. Acid Res. 17:2503 91989); "reverse transcriptase PCR" or "RT-PCR", "biotin capture PCR", "vectorette PCR". "panhandle PCR", and "PCR select cDNA subtraction", among others.

Strand displacement amplification (SDA) is generally described in Walker et al., in Molecular Methods for Virus Detection, Academic Press, Inc., 1995, and U.S. Pat. Nos. 5,455,166 and 5,130,238, all of which are hereby incorporated by reference.

Nucleic acid sequence based amplification (NASBA) is generally described in U.S. Pat. No. 5,409,818 and "Profiting from Gene-based Diagnostics", CTB International Publishing Inc., N.J., 1996, both of which are incorporated by reference.

Cycling probe technology (CPT) is a nucleic acid detection system based on signal or probe amplification rather than target amplification, such as is done in polymerase chain reactions (PCR). Cycling probe technology relies on a molar excess of labeled probe which contains a scissile linkage of RNA. Upon hybridization of the probe to the target, the resulting hybrid contains a portion of RNA:DNA. This area of RNA:DNA duplex is recognized by RNAseH and the RNA is excised, resulting in cleavage of the probe. The probe now consists of two smaller sequences which may be released, thus leaving the target intact for repeated rounds of the reaction. The unreacted probe is removed and the label is then detected. CPT is generally described in U.S. Pat. Nos. 5,011,769, 5,403,711, 5,660,988, and 4,876,187, and PCT published applications WO 95/05480, WO 95/1416, and WO 95/00667, all of which are specifically incorporated herein by reference.

The oligonucleotide ligation assay (OLA; sometimes referred to as the ligation chain reaction (LCR)) involve the ligation of at least two smaller probes into a single long probe, using the target sequence as the template for the ligase. See generally U.S. Pat. Nos. 5,185,243, 5,679,524 and 5,573,907; EP 0 320 308 B1; EP 0 336 731 B1; EP 0 439 182 B1; WO 90/01069; WO 89/12696; and WO 89/09835, all of which are incorporated by reference.

Invader™ technology is based on structure-specific polymerases that cleave nucleic acids in a site-specific manner. Two probes are used: an "invader" probe and a "signaling" probe, that adjacently hybridize to a target sequence with a non-complementary overlap. The enzyme cleaves at the overlap due to its recognition of the "tail", and releases the "tail" with a label. This can then be detected. The Invader™ technology is described in U.S. Pat. Nos. 5,846,717; 5,614,402; 5,719,028; 5,541,311; and 5,843,669, all of which are hereby incorporated by reference.

"Rolling circle amplification" is based on extension of a circular probe that has hybridized to a target sequence. A polymerase is added that extends the probe sequence. As the circular probe has no terminus, the polymerase repeatedly extends the circular probe resulting in concatamers of the circular probe. As such, the probe is amplified. Rolling-circle amplification is generally described in Baner et al. (1998) *Nuc. Acids Res.* 26:5073-5078; Barany, F. (1991) *Proc. Natl. Acad. Sci. USA* 88:189-193; and Lizardi et al. (1998) *Nat. Genet.* 19:225-232, all of which are incorporated by reference in their entirety.

"Branched DNA" signal amplification relies on the synthesis of branched nucleic acids, containing a multiplicity of nucleic acid "arms" that function to increase the amount of label that can be put onto one probe. This technology is generally described in U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference.

Similarly, dendrimers of nucleic acids serve to vastly increase the amount of label that can be added to a single molecule, using a similar idea but different compositions. This technology is as described in U.S. Pat. No. 5,175,270 and Nilsen et al., J. Theor. Biol. 187:273 (1997), both of which are incorporated herein by reference.

Recent focus has been on the analysis of the relationship between genetic variation and phenotype by making use of polymorphic DNA markers. Previous work utilized short tandem repeats (STRs) as polymorphic positional markers; however, recent focus is on the use of single nucleotide polymorphisms (SNPs), which occur at an average frequency of more than 1 per kilobase in human genomic DNA. Some SNPs, particularly those in and around coding sequences, are likely to be the direct cause of therapeutically relevant phenotypic variants and/or disease predisposition. Multiplex PCR amplification of SNP loci with subsequent hybridization to oligonucleotide arrays has been shown to be an accurate and reliable method of simultaneously genotyping at least hundreds of SNPs; see Wang et al., Science, 280:1077 (1998); see also Schafer et al., Nature Biotechnology 16:33-39 (1998). The compositions of the present invention facilitate multiplex assays.

There are a variety of particular techniques that are used to detect sequence, including mutations and SNPs. These include, but are not limited to, ligation based assays, cleavage based assays (mismatch and invasive cleavage such as Invader™), single base extension methods (see WO 92/15712, EP 0 371 437 B1, EP 0317 074 B1; Pastinen et al., Genome Res. 7:606-614 (1997); Syvänen, Clinica Chimica Acta 226:225-236 (1994); and WO 91/13075), and competitive probe analysis (e.g. competitive sequencing by hybridization; see below).

In addition, DNA sequencing is a crucial technology in biology today, as the rapid sequencing of genomes, including the human genome, is both a significant goal and a significant hurdle. Thus there is a significant need for robust, high-throughput methods. Traditionally, the most common method of DNA sequencing has been based on polyacrylamide gel fractionation to resolve a population of chain-terminated fragments (Sanger et al., Proc. Natl. Acad. Sci. USA 74:5463 (1977); Maxam & Gilbert). The population of fragments, terminated at each position in the DNA sequence, can be generated in a number of ways. Typically, DNA polymerase is used to incorporate dideoxynucleotides that serve as chain terminators.

Several alternative methods have been developed to increase the speed and ease of DNA sequencing. For example, sequencing by hybridization has been described (Drmanac et al., Genomics 4:114 (1989); Koster et al., Nature Biotechnology 14:1123 (1996); U.S. Pat. Nos. 5,525,464; 5,202,231 and 5,695,940, among others). Similarly, sequencing by synthesis is an alternative to gel-based sequencing. These methods add and read only one base (or at most a few bases, typically of the same type) prior to polymerization of the next base. This can be referred to as "time resolved" sequencing, to contrast from "gel-resolved" sequencing. Sequencing by synthesis has been described in U.S. Pat. No. 4,971,903 and Hyman, Anal. Biochem. 174:423 (1988); Rosenthal, International Patent Application Publication 761107 (1989); Metzker et al., Nucl. Acids Res. 22:4259 (1994); Jones, Biotechniques 22:938 (1997); Ronaghi et al., Anal. Biochem. 242:84 (1996), Nyren et al., Anal. Biochem. 151:504 (1985). Detection of ATP sulfurylase activity is described in Karamohamed and Nyren, Anal. Biochem. 271:81 (1999).

Sequencing using reversible chain terminating nucleotides is described in U.S. Pat. Nos. 5,902,723 and 5,547,839, and Canard and Arzumanov, Gene 11:1 (1994), and Dyatkina and Arzumanov, Nucleic Acids Symp Ser 18:117 (1987). Reversible chain termination with DNA ligase is described in U.S. Pat. No. 5,403,708. Time resolved sequencing is described in Johnson et al., Anal. Biochem. 136:192 (1984). Single molecule analysis is described in U.S. Pat. No. 5,795,782 and Elgen and Rigler, Proc. Natl. Acad Sci USA 91(13):5740 (1994), all of which are hereby expressly incorporated by reference in their entirety.

One promising sequencing by synthesis method is based on the detection of the pyrophosphate (PPi) released during the DNA polymerase reaction. As nucleotriphosphates are added to a growing nucleic acid chain, they release PPi. This release can be quantitatively measured by the conversion of PPi to ATP by the enzyme sulfurylase, and the subsequent production of visible light by firefly luciferase.

Several assay systems have been described that capitalize on this mechanism. See for example WO93/23564, WO 98/28440 and WO98/13523, all of which are expressly incorporated by reference. A preferred method is described in Ronaghi et al., Science 281:363 (1998). In this method, the four deoxynucleotides (dATP, dGTP, dCTP and dTTP; collectively dNTPs) are added stepwise to a partial duplex comprising a sequencing primer hybridized to a single stranded DNA template and incubated with DNA polymerase, ATP sulfurylase, luciferase, and optionally a nucleotide-degrading enzyme such as apyrase. A dNTP is only incorporated into the growing DNA strand if it is complementary to the base in the template strand. The synthesis of DNA is accompanied by the release of PPi equal in molarity to the incorporated dNTP. The PPi is converted to ATP and the light generated by the luciferase is directly proportional to the amount of ATP. In some cases the unincorporated dNTPs and the produced ATP are degraded between each cycle by the nucleotide degrading enzyme.

In some cases the DNA template is associated with a solid support. To this end, there are a wide variety of known methods of attaching DNAs to solid supports. Recent work has focused on the attachment of binding ligands, including nucleic acid probes, to microspheres that are randomly distributed on a surface, including a fiber optic bundle, to form high density arrays. See for example PCTs US98/21193, PCT US99/14387 and PCT US98/05025; WO98/50782; and U.S. Ser. Nos. 09/287,573, 09/151,877, 09/256,943, 09/316,154, 60/119,323, 09/315,584; all of which are expressly incorporated by reference.

An additional technique utilizes sequencing by hybridization. For example, sequencing by hybridization has been described (Drmanac et al., Genomics 4:114 (1989); U.S. Pat. Nos. 5,525,464; 5,202,231 and 5,695,940, among others, all of which are hereby expressly incorporated by reference in their entirety).

In addition, sequencing using mass spectrometry techniques has been described; see Koster et al., Nature Biotechnology 14:1123 (1996).

Finally, the use of adapter-type sequences that allow the use of universal arrays has been described in limited contexts; see for example Chee et al., Nucl. Acid Res. 19:3301 (1991); Shoemaker et al., Nature Genetics 14:450 (1998); Barany, F. (1991) Proc. Natl. Acad. Sci. USA 88:189-193; EP 0 799 897 A1; WO 97/31256, all of which are expressly incorporated by reference.

PCTs US98/21193, PCT US99/14387 and PCT US98/05025; WO98/50782; and U.S. Ser. Nos. 09/287,573, 09/151,877, 09/256,943, 09/316,154, 60/119,323, 09/315,584; all of which are expressly incorporated by reference, describe novel compositions utilizing substrates with microsphere arrays, which allow for novel detection methods of nucleic acid hybridization.

A common feature of all of these assays and techniques is the requirement for a large number of oligonucleotides. In addition, as multiplex experiments are performed, solutions containing multiple types of oligonucleotides must be prepared.

The prior art describes methods of synthesizing oligonucleotides. Generally, synthesis methods can be divided into directed and non-directed methods. For non-directed, combinatorial methods, bead-based or tea bag synthesis methods have been described using split and mix procedures. Split and mix synthesis is described in Peptide and Peptidomimetic Libraries, Molecular Biotechnology, Vol. 9, 1998, which ex expressly incorporated herein by reference. A limitation of this method is that all combinations of polymers are synthesized.

Alternatively, the prior art describes directed synthesis methods in which a particular polymer is separated from other polymers during the synthesis process. A limitation to this approach is the necessity for separate reactions and the requirement to mix the polymers together to form pools of oligonucleotides.

Accordingly, it is an object of the present invention to provide compositions and methods for generating a pool of oligonucleotides.

SUMMARY OF THE INVENTION

In accordance with the objects outlined above, the present invention provides methods of generating pools of oligonucleotides. The methods include providing a substrate and at least first and second different oligonucleotides linked to said substrate through first and second cleavable linkers, respectively. In addition, the method includes cleaving the first and second linkers, thereby releasing the first and second oligonucleotides from the substrate thereby generating a pool of oligonucleotides comprising the first and second oligonucleotides.

In an additional aspect the invention includes a method for generating a pool of oligonucleotides comprising providing an array comprising a substrate and a population of oligonucleotides. The population comprises at least first and second subpopulations. The subpopulations comprise at least first and second different oligonucleotides of known sequence. The first and second oligonucleotides are immobilized to first and second beads, respectively, through first and second cleavable linkers, respectively. The first and second beads are distributed on the substrate. Subsequently, the first and second linkers are cleaved thereby releasing the first and second subpopulations from the first and second beads, thereby generating a pool of oligonucleotides comprising the first and second oligonucleotides.

In an additional aspect the invention includes a method for generating a pool of oligonucleotides comprising providing an array comprising a substrate and a population of oligonucleotides. The population comprises at least first and second subpopulations. The subpopulations comprise at least first and second different oligonucleotides of known sequence. The first and second oligonucleotides are immobilized to a chip through first and second cleavable linkers, respectively. The first and second linkers are cleaved thereby releasing the first and second subpopulations from the chip, thereby generating a pool of oligonucleotides comprising the first and second oligonucleotides.

In addition the invention includes a composition comprising a substrate and at least first and second different oligonucleotides of known sequence linked to the substrate through first and second cleavable linkers, respectively. The composition also includes at least one linker cleaving agent.

In addition the invention includes a kit comprising a substrate and at least first and second different oligonucleotides of known sequence linked to the substrate through first and second cleavable linkers, respectively. The kit also includes at least one linker cleaving agent.

BRIEF DESCRIPTION OF THE DRAWINGS

FIG. 1 Depicts an embodiment of a method of generating a pool of oligonucleotides. Different subpopulations of oligonucleotides 10, 11 and 12 are immobilized on a substrate 20 by a cleavable linker 5. Following the addition of a cleavage agent, the oligonucleotides 10, 11 and 12 are released into the solution phase.

FIG. 2 depicts an embodiment of a method of generating a pool of oligonucleotides. Different subpopulations of oligonucleotides 10, 11 and 12 are immobilized on a substrate 20 by different cleavable linkers 5, 6 and 7. Following the addition of multiple site-specific cleavage agents, the oligonucleotides immobilized by the respective linkers are released into the solution phase.

FIG. 3 depicts an embodiment of a method of generating a pool of oligonucleotides. Different subpopulations of oligonucleotides 10, 11, 12 and 13 are immobilized to an association moiety 30 via a linker 5. The association moiety 30 is distributed in wells 21 in the substrate 20. Following the addition of a cleavage agent, the oligonucleotides 10, 11, 12 and 13 are released into the solution phase.

DETAILED DESCRIPTION OF THE INVENTION

The present invention is directed to compositions and methods for preparing oligonucleotide solutions. In particular the invention includes preparing an array of oligonucleotides. The oligonucleotides are attached either directly or indirectly to a substrate through a cleavable linker. Upon cleavage of the linker, a pool of oligonucleotides is formed. Pools of oligonucleotides find use in a number of solution-phase nucleic acid detection and/or amplification reactions.

Accordingly the present invention provides compositions and methods for generating pools of oligonucleotides. The method includes providing a substrate and a plurality of oligonucleotides attached to the substrate by a cleavable linker and then cleaving the linker to release the oligonucleotides from the substrate thereby generating a pool of oligonucleotides.

In one embodiment the oligonucleotide is directly attached to the substrate via a cleavable linker. In an alternative embodiment, the oligonucleotide is indirectly attached to the substrate. In this embodiment, the oligonucleotide is attached to an association moiety via a linker. The association moiety is then distributed on the substrate.

By "pool" is meant a plurality or more than one solution-phase oligonucleotide. Preferably, a pool includes two or more different oligonucleotides. More preferably a pool includes 20 or more different oligonucleotides. Most preferably a pool includes greater than 50 different oligonucleotides.

By "population" herein is meant a plurality of oligonucleotides. In one embodiment, within the population are separate subpopulations, which can be a single oligonucleotide or multiple identical oligonucleotides. That is, the oligonucleotides within a subpopulation are the same. Alternatively, a subpopulation may be defined by the linker. That is, in this embodiment, each subpopulation can be defined by the linker used to immobilize the oligonucleotide to the substrate and/or association moiety. That is, in this embodiment, the linkers within a subpopulation are the same. In one embodiment when the linkers within a subpopulation are the same, the oligonucleotides within the subpopulation are the same; in an alternative embodiment the oligonucleotides within the subpopulation need not be the same.

By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644, 048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386, 023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done to facilitate the addition of labels, or to increase the stability and half-life of such molecules in physiological environments.

As will be appreciated by those in the art, all of these nucleic acid analogs may find use in the present invention. In addition, mixtures of naturally occurring nucleic acids and analogs can be made. Alternatively, mixtures of different nucleic acid analogs, and mixtures of naturally occurring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2-4° C. drop in Tm for an internal mismatch. With the non-ionic PNA backbone, the drop is closer to 7-9° C. This allows for better detection of mismatches. Similarly, due to their non-ionic nature, hybridization of the bases attached to these backbones is relatively insensitive to salt concentration.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. A preferred embodiment utilizes isocytosine and isoguanine in nucleic acids designed to be complementary to other probes, rather than target sequences, as this reduces non-specific hybridization, as is generally described in U.S. Pat. No. 5,681,702. As used herein, the term "nucleoside" includes nucleotides as well as nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

The oligonucleotides can be of any length although in a preferred embodiment they are from 2 to 200 nucleotides in length, in a preferred embodiment they are from 5 to 100 nucleotides in length and in a particularly preferred embodiment they are from 7 to 50 nucleotides in length.

In a preferred embodiment the oligonucleotide is attached to the substrate via linker. That is, when attached to a substrate or association moiety, the oligonucleotide is bound or conjugated to a cleavable linker. By "cleavable linker" is meant a linker that is susceptible to cleavage with a specific agent and mediates binding of the substrate and/or the association moiety to the oligonucleotide. In one embodiment the linker is part of the nucleic acid. Alternatively, the linker can be a modification of the nucleic acid. Alternatively, the linker is an additional moiety.

Generally, the linker is separable or distinct from the region of the molecule comprising the desired oligonucleotide. That is, upon cleavage of the linker, the nature i.e. structure or sequence of the desired oligonucleotide is not altered. However, in some embodiments the structure or sequence of the oligonucleotide is altered.

In one embodiment the oligonucleotide is linked directly to a substrate through the linker. In an alternative embodiment the oligonucleotide is indirectly linked to the substrate, for example by attachment of the linker to a bead.

A cleavable linker is susceptible to cleavage with agents such as but not limited to light, base, acid and enzymes such as sequence specific restriction enzymes or proteases. In a preferred embodiment the linker is a nucleotide linker and comprises a site for cleavage by a sequence specific restriction endonuclease. In an additionally preferred embodiment the restriction site is a substrate for a "rare-cutting" enzyme. Rare-cutting restriction endonucleases are known in the art and include, for example, those enzymes that recognize 6 or more nucleotides. In some instances it is preferable to use more frequent restriction sites such as those that contain a 2, 3, 4 or 5 nucleotide recognition sequence.

In a preferred embodiment when the linker is an oligonucleotide, the linker sequences do not have significant homology to the oligonucleotide to which they are attached. That is, the linker sequences are substantially unique relative to the oligonucleotides. Thus, in this embodiment, the linker sequences can be specifically cleaved relative to the oligonucleotides. Cleavage of the linker results in release of the oligonucleotides into the solution-phase to form a pool of oligonucleotides.

Accordingly, preferred embodiments utilize some method to select useful linker sequences. Such methods include the use of computer searching or comparison programs to find unique cleavage sequences relative to the oligonucleotide sequence. Sequence comparisons are known in the art and include, but are not limited to, the local homology algorithm of Smith & Waterman, Adv. Appl. Math. 2:482 (1981), by the homology alignment algorith of Needleman & Wunsch, J. Mol. Biool. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387-395 (1984), preferably using the default settings, or by inspection.

The linker sequences are added to the oligonucleotides in a variety of ways, as will be appreciated by those in the art. In one embodiment, the linker sequence and oligonucleotide are synthesized contiguously. That is, using standard oligonucleotide synthesis methods, the oligonucleotide and linker are synthesized as one continuous oligonucleotide.

In an alternative embodiment, nucleic acid amplification reactions are done, as is generally outlined in "Detection of Nucleic Acid Amplification Reactions Using Bead Arrays" and "Sequence Determination of Nucleic Acids using Arrays with Microspheres" both of which were filed on Oct. 22, 1999, (U.S. Ser. Nos. 60/161,148 and 09/425,633, respectively), and "Detection of Nucleic Acid Reactions on Bead Arrays" filed on Apr. 20, 2000, and Apr. 21, 2000 (U.S. Ser. Nos. 09/553,993 and 09/556,463, respectively), all of which are hereby incorporated by reference in their entirety. In general, the techniques can be described as follows. Most amplification techniques require one or more primers hybridizing to the target sequence. The linker sequences can be added to one or more primers that are complementary to the oligonucleotide to which the linker is to be added (depending on the configuration/orientation of the system and need) and the amplification reactions are run. Thus, for example, PCR primers comprising at least one linker sequence may be used.

In an alternative embodiment, non-nucleic acid reactions are used to add linker sequences to the oligonucleotides. In this embodiment, binding partner pairs or chemical methods may be used. For example, one member of a binding partner pair may be attached to the linker sequence and the other member attached to the oligonucleotide. For example, the binding partner can be a hapten or antigen, which will bind its binding partner. For example, suitable binding partner pairs include, but are not limited to: antigens (such as proteins (including peptides)) and antibodies (including fragments thereof (FAbs, etc.)); proteins and small molecules, including biotin/streptavidin and digoxygenin and antibodies; enzymes and substrates or inhibitors; other protein-protein interacting pairs; receptor-ligands; and carbohydrates and their binding partners, are also suitable binding pairs. Nucleic acid—nucleic acid binding proteins pairs are also useful. Preferred binding partner pairs include, but are not limited to, biotin (or imino-biotin) and streptavidin, digeoxinin and Abs, and Pro-linx™ reagents.

In a preferred embodiment, chemical attachment methods are used. In this embodiment, chemical functional groups on each of the oligonucleotides and linker sequences are used. As is known in the art, this may be accomplished in a variety of ways. Preferred functional groups for attachment are amino groups, carboxy groups, oxo groups and thiol groups, with amino groups being particularly preferred. Using these functional groups, the two sequences are joined together; for example, amino groups on each nucleic acid may be attached, for example using linkers as are known in the art; for example, homo- or hetero-bifunctional linkers as are well known (see 1994 Pierce Chemical Company catalog, technical section on cross-linkers, pages 155-200, incorporated herein by reference).

In a preferred embodiment, aptamers are used in the system. Aptamers are nucleic acids that can be made to bind to virtually any target; see Bock et al., Nature 355:564 (1992); Femulok et al., Current Op. Chem. Biol. 2:230 (1998); and U.S. Pat. Nos. 5,270,163, 5,475,096, 5,567,588, 5,595,877, 5,637,459, 5,683,867, 5,705,337, and related patents, all of which are expressly incorporated herein by reference.

In one embodiment linkers are added prior to immobilization to the substrate and/or bead. That is, a linker-conjugated or linker-bound oligonucleotide is attached to the substrate or association moiety. In an alternative embodiment, the oligonucleotide is attached to the linker while the linker is immobilized to the substrate or association moiety. Accordingly, when describing attachment of nucleic acids to a substrate or association moiety and attachment of linker-bound or linker-conjugated oligonucleotides to a substrate or association moiety it is understood that linkers mediate the attachment.

In addition, the present invention is directed to the use of linker sequences to assemble arrays comprising other molecules. That is, cleavable linkers can be used to assemble arrays of molecules other than oligonucleotides. Other molecules include but are not limited to other polymers. Thus, upon cleavage of the linker, pools of solution-phase polymers are generated. Such polymers include but are not limited to peptides, polysaccharides, polymers of small molecules and the like.

In an alternative embodiment the linker comprises amino acids and thus forms a peptide linker. Peptide linkers are cleaved by agents that include but are not limited to proteases or chemicals including bases, acids or CNBr.

In one embodiment, the oligonucleotides comprise labels. By "label" or "detectable label" herein is meant a moiety that allows detection. This may be a primary label or a secondary label. Accordingly, detection labels may be primary labels (i.e. directly detectable) or secondary labels (indirectly detectable).

In a preferred embodiment, the detection label is a primary label. A primary label is one that can be directly detected, such as a fluorophore. In general, labels fall into three classes: a) isotopic labels, which may be radioactive or heavy isotopes; b) magnetic, electrical, thermal labels; and c) colored or luminescent dyes. Labels can also include enzymes (horseradish peroxidase, etc.) and magnetic particles. Preferred labels include chromophores or phosphors but are preferably fluorescent dyes. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, quantum dots (also referred to as "nanocrystals": see U.S. Ser. No. 09/315,584, hereby incorporated by reference), pyrene, Malacite green, stilbene, Lucifer Yellow, Cascade Blue™, Texas Red, Cy dyes (Cy3, Cy5, etc.), alexa dyes, phycoerythin, bodipy, and others described in the 6th Edition of the Molecular Probes Handbook by Richard P. Haugland, hereby expressly incorporated by reference.

In a preferred embodiment, a secondary detectable label is used. A secondary label is one that is indirectly detected; for example, a secondary label can bind or react with a primary label for detection, can act on an additional product to generate a primary label (e.g. enzymes), or may allow the separation of the compound comprising the secondary label from unlabeled materials, etc. Secondary labels find particular use in systems requiring separation of labeled and unlabeled probes, such as SBE, OLA, invasive cleavage reactions, etc; in addition, these techniques may be used with many of the other techniques described herein. Secondary labels include, but are not limited to, one of a binding partner pair; chemically modifiable moieties; nuclease inhibitors, enzymes such as horseradish peroxidase, alkaline phosphatases, luciferases, etc.

In a preferred embodiment, the secondary label is a binding partner pair. For example, the label may be a hapten or antigen, which will bind its binding partner. For example, suitable binding partner pairs include, but are not limited to: antigens (such as proteins (including peptides)) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid—nucleic acid binding proteins pairs are also useful. Preferred binding partner pairs include, but are not limited to, biotin (or imino-biotin) and streptavidin, digeoxinin and Abs, and Prolinx™ reagents (see www.prolinxinc.com/ie4/home.hmtl).

In a preferred embodiment, the binding partner pair comprises biotin or imino-biotin and streptavidin. Imino-biotin is particularly preferred as imino-biotin disassociates from streptavidin in pH 4.0 buffer while biotin requires harsh denaturants (e.g. 6 M guanidinium HCl, pH 1.5 or 90% formamide at 95° C.).

In a preferred embodiment, the binding partner pair comprises a primary detection label and an antibody that will specifically bind to the primary detection label. By "specifically bind" herein is meant that the partners bind with specificity sufficient to differentiate between the pair and other components or contaminants of the system. The binding should be sufficient to remain bound under the conditions of the assay, including wash steps to remove non-specific binding. In some embodiments, the dissociation constants of the pair will be less than about $10^{-4}$-$10^{-6}$ $M^{-1}$, with less than about $10^{-5}$ to $10^{-9}$ $M^{-1}$ being preferred and less than about $10^{-7}$-$10^{-9}$ $M^{-1}$ being particularly preferred.

In a preferred embodiment, the secondary label is a chemically modifiable moiety. In this embodiment, labels comprising reactive functional groups are incorporated into the nucleic acid. The functional group can then be subsequently labeled with a primary label. Suitable functional groups include, but are not limited to, amino groups, carboxy groups, maleimide groups, oxo groups and thiol groups, with amino groups and thiol groups being particularly preferred. For example, primary labels containing amino groups can be attached to secondary labels comprising amino groups, for example using linkers as are known in the art; for example, homo- or hetero-bifunctional linkers as are well known (see 1994 Pierce Chemical Company catalog, technical section on cross-linkers, pages 155-200, incorporated herein by reference).

Thus, when labeled oligonucleotides are synthesized on an array or synthesized and associated with a substrate, labeled arrays are formed. In a preferred embodiment, each member of a population of oligonucleotides is labeled with the same label. In an alternative embodiment each member of a subpopulation of oligonucleotides is labeled with the same label. That is, in making the labeled array, the label serves to identify the oligonucleotide to which it is attached. In a sense, the label serves as a code for the sequence of the oligonucleotide.

In a preferred embodiment, the oligonucleotide is attached directly to the substrate as is described in more detail herein. Alternatively, the oligonucleotide is indirectly associated with the substrate. That is, the oligonucleotide associates with the substrate via an association moiety as described herein.

By "substrate" or "solid support" or other grammatical equivalents herein is meant any material that can be modified for the attachment or association of nucleic acids. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses, plastics, optical fiber bundles, and a variety of other polymers.

By "association moiety" (AM) is meant any material to which an oligonucleotide can be attached that serves as an intermediate for association of an oligonucleotide to a substrate. As will be appreciated by those in the art, the number of possible AMs is large. Possible AMs include any number of solid supports such as beads or microspheres.

Generally the substrate is flat (planar), although as will be appreciated by those in the art, other configurations of substrates may be used as well; for example, when oligonucleotides are associated with the substrate via a bead as described below, three dimensional configurations can be used, for example by embedding the beads in a porous block of plastic that allows sample or reagent access to the beads. Similarly, the beads may be placed on the inside surface of a tube, for flow-through sample analysis to minimize sample or reagent volume. Preferred substrates include optical fiber bundles as discussed below, and flat planar substrates such as glass, polystyrene and other plastics and acrylics.

In a preferred embodiment the substrate is a chip or biochip. By "chip" or "biochip" herein is meant a planar substrate to which nucleic acids are directly or indirectly attached. In a preferred embodiment, the surface of the biochip and the nucleic acid may be derivatized with chemical functional groups for subsequent attachment of the two. Thus, for example, the biochip is derivatized with a chemical functional group including, but not limited to, amino groups, carboxy groups, oxo groups and thiol groups, with amino groups being particularly preferred. Using these functional groups, the oligonucleotides can be attached using functional groups on the oligonucleotides. For example, nucleic acids containing amino groups can be attached to surfaces comprising amino groups, for example using linkers as are known in the art; for example, homo- or hetero-bifunctional linkers as are well known (see 1994 Pierce Chemical Company catalog, technical section on cross-linkers, pages 155-200, incorporated herein by reference). In addition, in some cases, additional linkers, such as alkyl groups (including substituted and heteroalkyl groups) may be used.

In one embodiment, the substrate is an optical fiber bundle or array, as is generally described in U.S. Ser. Nos. 08/944, 850 and 08/519,062, PCT US98/05025, and PCT US98/09163, all of which are expressly incorporated herein by reference. Preferred embodiments utilize preformed unitary fiber optic arrays. By "preformed unitary fiber optic array" herein is meant an array of discrete individual fiber optic strands that are co-axially disposed and joined along their lengths. The fiber strands are generally individually clad. However, one thing that distinguished a preformed unitary array from other fiber optic formats is that the fibers are not individually physically manipulatable; that is, one strand generally cannot be physically separated at any point along its length from another fiber strand.

In one embodiment at least one surface of the substrate is modified to contain discrete, individual sites for later association of nucleic acids or oligonucleotides. These sites may comprise physically altered sites, i.e. physical configurations such as wells or small depressions in the substrate that can retain AMs such as beads, such that a microsphere can rest in the well, or the use of other forces (magnetic or compressive), or chemically altered or active sites, such as chemically functionalized sites, electrostatically altered sites, hydrophobically/hydrophilically functionalized sites, spots of adhesive, etc.

The sites may be arranged in a pattern, i.e. a regular design or configuration, or randomly distributed. A preferred embodiment utilizes a regular pattern of sites such that the sites may be addressed in the X-Y coordinate plane. "Pattern" in this sense includes a repeating unit cell, preferably one that allows a high density of nucleic acids on the substrate. However, it should be noted that these sites may not be discrete sites. That is, it is possible to use a uniform surface of adhesive or chemical functionalities, for example, that allows the attachment of nucleic acids at any position. That is, the surface of the substrate is modified to allow attachment of the nucleic acids at individual sites, whether or not those sites are contiguous or non-contiguous with other sites. Thus, the surface of the substrate may be modified such that discrete sites are formed that can retain a single nucleic acid, or alternatively, the surface of the substrate is modified and nucleic acids, for example, when attached to beads may be placed anywhere, but eventually end up at discrete sites.

In a preferred embodiment, the surface of the substrate is modified to contain wells, i.e. depressions in the surface of the substrate. This may be done as is generally known in the art using a variety of techniques, including, but not limited to, photolithography, stamping techniques, molding techniques and microetching techniques. As will be appreciated by those in the art, the technique used will depend on the composition and shape of the substrate and the nature of any association moieties to be used, if any.

In a preferred embodiment, physical alterations are made in a surface of the substrate to produce the sites. In a preferred embodiment, the substrate is a fiber optic bundle and the surface of the substrate is a terminal end of the fiber bundle, as is generally described in U.S. Pat. No. 6,023,540 and U.S. Ser. No. 09/151,877, both of which are hereby expressly incorporated by reference. In this embodiment, wells are made in a terminal or distal end of a fiber optic bundle comprising individual fibers. In this embodiment, the cores of the individual fibers are etched, with respect to the cladding, such that small wells or depressions are formed at one end of the fibers. The required depth of the wells will depend on the size of the moiety i.e. beads, to be added to the wells.

Generally in this embodiment, the microspheres or beads are non-covalently associated in the wells, although the wells may additionally be chemically functionalized as is generally described below, cross-linking agents may be used, or a physical barrier may be used, i.e. a film or membrane over the beads.

By "microspheres" or "beads" or "particles" or grammatical equivalents herein is meant small discrete particles. The composition of the beads will vary, depending on the class of oligonucleotide and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon may all be used. "*Microsphere Detection Guide*" from Bangs Laboratories, Fishers Ind. is a helpful guide.

The beads need not be spherical; irregular particles may be used. In addition, the beads may be porous, thus increasing the surface area of the bead available for either capture probe attachment or tag attachment. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller beads may be used.

It should be noted that when beads are used, a key component of the invention is the use of a substrate/bead pairing that allows the association or attachment of the beads at discrete sites on the surface of the substrate, such that the beads do not move or dislodge during the course of the assembly or cleavage.

Attachment of the nucleic acids to the substrate may be done in a variety of ways, as will be appreciated by those in the art, including, but not limited to, chemical or affinity capture (for example, including the incorporation of derivatized nucleotides such as AminoLink or biotinylated nucleotides that can then be used to attach the nucleic acid to a surface, as well as affinity capture by hybridization), cross-linking, and electrostatic attachment, etc. In a preferred embodiment, affinity capture is used to attach the nucleic acids to the substrate. For example, nucleic acids can be derivatized, for example with one member of a binding pair, and the substrate or association moiety derivatized with the other member of a binding pair. Suitable binding pairs include complementary nucleic acids. In addition, the nucleic acids may be biotinylated (for example using enzymatic incorporate of biotinylated nucleotides, for by photoactivated cross-linking of biotin). Biotinylated nucleic acids can then be captured on streptavidin-coated substrate or beads, as is known in the art. Similarly, other hapten-receptor combinations can be used, such as digoxigenin and anti-digoxigenin antibodies. Alternatively, chemical groups can be added in the form of derivatized nucleotides, that can them be used to add the nucleic acid to the surface.

In this embodiment, the oligonucleotides are previously synthesized as is known in the art, and then attached to the surface of the solid support. As will be appreciated by those skilled in the art, either the 5' or 3' terminus may be attached to the solid support, or attachment may be via an internal nucleoside.

Preferred attachments are covalent, although even relatively weak interactions (i.e. non-covalent) can be sufficient to attach a nucleic acid to a surface. Thus, for example, electrostatic interactions can be used for attachment, for example by having substrates carrying the opposite charge to the oligonucleotide.

Similarly, affinity capture utilizing hybridization can be used to attach nucleic acids to substrates or association moieties. For example, as is known in the art, polyA+ RNA is routinely captured by hybridization to oligo-dT beads; this may include oligo-dT capture followed by a cross-linking step, such as psoralen crosslinking). If the nucleic acids of interest do not contain a polyA tract, one can be attached by polymerization with terminal transferase, or via ligation of an oligoA linker, as is known in the art.

Alternatively, chemical crosslinking may be used to attach nucleic acids to the substrate, for example by photoactivated crosslinking of thymidine to reactive groups, as is known in the art.

In a preferred embodiment, the surface of the substrate is modified to contain chemically modified sites, that can be used to attach, either covalently or non-covalently, the nucleic acids of the invention to the discrete sites or locations on the substrate. "Chemically modified sites" in this context includes, but is not limited to, the addition of a pattern of chemical functional groups including amino groups, carboxy groups, oxo groups and thiol groups, that can be used to attach nucleic acids, which generally also contain corresponding reactive functional groups; the addition of a pattern of charged groups (similar to the chemical functionalities) for the electrostatic attachment of the nucleic acids, i.e. when the nucleic acids comprise charged groups opposite to the sites. As outlined above, "pattern" in this sense includes the use of a uniform treatment of the surface to allow attachment of the nucleic acids at discrete sites, as well as treatment of the surface resulting in discrete sites. As will be appreciated by those in the art, this may be accomplished in a variety of ways.

Alternatively, the oligonucleotides may be synthesized in situ on the substrate, as is known in the art. For example, photoactivation techniques utilizing photopolymerization compounds and techniques are used. In a preferred embodiment, the nucleic acids can be synthesized in situ using well known photolithographic techniques, such as those described in WO 95/25116; WO 95/35505; U.S. Pat. Nos. 5,700,637 and 5,445,934; and references cited within, all of which are expressly incorporated by reference; these methods of attachment form the basis of the Affymetrix GeneChip™ technology.

Alternatively, the oligonucleotides may be synthesized on the substrate using printing technology as described in U.S. Pat. No. 5,831,070, which is expressly incorporated herein by reference. Alternatively, the oligonucleotides may be synthesized by spotting as described in U.S. Pat. No. 5,807,522 which is expressly incorporated herein by reference.

In an alternative embodiment the oligonucleotides are synthesized on association moieties or solid support such as microspheres that are then distributed on a substrate. As is known in the art, many classes of chemical compounds are currently synthesized on solid supports, such as peptides, organic moieties, and nucleic acids. It is a relatively straightforward matter to adjust the current synthetic techniques to use beads.

In one embodiment the oligonucleotides are synthesized randomly i.e. with no bias or restriction at any of the positions in the oligonucleotide. That is, synthesis is non-directed. As such, pools comprising random oligonucleotides are generated by the method. Methods of randomly synthesizing oligonucleotides are known in the art and as described in U.S. Pat. No. 5,504,190, which is expressly incorporated herein by reference. Other combinatorial techniques are summarized in Peptide and, Peptidomimetic Libraries, Molecular Biotechnology, Vol. 9, 1998, which ex expressly incorporated herein by reference.

In an alternative embodiment, the oligonucleotides are not randomly produced, but rather are synthesized with an eye to targeting a particular molecule. That is, synthesis of the oligonucleotides is directed. As is known in the art, oligonucleotides hybridize with a complementary strand; thus, the oligonucleotides are designed to target a particular complementary molecule. This complementarity need not be perfect; there may be any number of base pair mismatches that will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under the selected reaction conditions.

In one embodiment oligonucleotides are designed to hybridize with DNA, for example, for genotyping, single nucleotide polymorphism (SNP) detection or for use as primers in amplification, in particular multi-plex amplification, reactions.

Alternatively, oligonucleotides are synthesized with only certain degenerate positions. That is, some of the positions are fixed or biased for a particular nucleotide while other positions are degenerate or synthesized with random nucleotides.

Accordingly the present invention provides array compositions comprising a substrate comprising oligonucleotides and a linker. By "array" herein is meant a plurality of nucleic acids in an array format; the size of the array will depend on the composition and end use of the array. Nucleic acids arrays are known in the art, and can be classified in a number of ways; both ordered arrays (e.g. the ability to resolve chemistries at discrete sites), and random arrays are included. Ordered arrays include, but are not limited to, those made using photolithography techniques (Affymetrix GeneChip™), spotting techniques (Synteni and others), printing techniques (Hewlett Packard and Rosetta), three dimensional "gel pad" arrays, etc.

In a preferred embodiment the array compositions further comprise a linker cleaving agent. As described herein, linker cleaving agents include but are not limited to light, chemicals including base and acid, enzymes such as proteases and nucleases. In a particularly preferred embodiment the nucleases include sequence specific restriction endonucleases as are known in the art and described herein. Additional cleavage agents are described in Promega Catalog, 1997, pp. 293-297 and 34-74, and Pierce Catalog and Handbook, 1994, pp. O-209 to O-221, both of which are expressly incorporated herein by reference.

In an additional embodiment, the compositions further comprise solution-phase oligonucleotides. That is, once cleavage of the linker has begun and the oligonucleotides are cleaved from the substrate, the oligonucleotides are released into the solution-phase. Accordingly, a pool of oligonucleotides in solution is formed.

Once formed, the array of oligonucleotides finds use in a number of aspects. In a particularly preferred embodiment the arrays are contacted with a cleaving agent that cleaves the linker. That is, the substrate to which the population oligonucleotides is attached is contacted with a cleaving agent thereby releasing the oligonucleotides into the solution phase (FIG. 1). As one of ordinary skill in the art appreciates cleavage conditions will vary with the nature of the cleavage agent. Generally, when cleavage agents are enzymes, conditions will vary with respect to metal, temperature, pH and salt concentration. The duration or time of cleavage reactions also will vary depending on the cleavage agent selected.

In an alternative embodiment, the cleaving agent recognizes only a subset of linkers. That is, as described above, each subpopulation of oligonucleotides contains a different linker. Accordingly, incubation of the array with a particular site-specific cleaving agent results in release of only the oligonucleotide immobilized with the respective linker (FIG. 2). Moreover, incubation with multiple site-specific cleaving agents results in the release of multiple subpopulations of oligonucleotides.

In an alternative embodiment, the oligonucleotides are indirectly attached to the substrate. That is, linkers can immobilize the oligonucleotides either directly to the substrate or indirectly. When indirectly attached to the substrate, oligonucleotides are attached to AMs via linkers as outlined herein. The AMs are distributed on the substrate forming an array. Subsequently, the array is contacted with a cleaving agent as described herein resulting in the release of the oligonucleotides into the solution phase (FIG. 3).

In an additional embodiment, the array of oligonucleotides finds use in kits. That is, kits can be formulated to include an array of oligonucleotides. As described herein, the oligonucleotides may comprise random oligonucleotides; alternatively, the oligonucleotides may comprise known sequences. In addition, the oligonucleotides may comprise a label. In this embodiment, the kit comprises a labeled array.

The kit also includes a linker cleaving agent. That is, to facilitate the formation of a pool of oligonucleotides, the kit includes at least one but may also include as many cleaving agents as necessary to release the desired oligonucleotides from the substrate.

In addition, the kit may also include at least one control oligonucleotide. The control oligonucleotide is designed to be complementary to a subpopulation of immobilized oligonucleotides or a population of control immobilized oligonucleotides. In a preferred embodiment the control oligonucleotide comprises a label as described herein.

In one embodiment the control oligonucleotide finds use in determining the quality of the array of oligonucleotides. That is, in one embodiment, the control oligonucleotide is contacted with the array of oligonucleotides prior to cleavage of the linkers. The labeled control oligonucleotide is then detected, for example by viewing the array under a microscope. Other detection methods are described in more detail in U.S. Ser. No. 09/556,463, filed Apr. 21, 2000, which is expressly incorporated herein by reference. The presence of the label provides an indication of the quality or identity of the array. As such, the array of oligonucleotides also facilitates sample handling, tracking and storage.

Once formed, the pool of oligonucleotides finds use in a number of assays. In addition, as nucleic acid experiments are performed in multiplex, a solution that contains many types of oligonucleotides must be prepared. Examples of experiments that may require pools of oligonucleotides when performed in solution include assays for genotyping, such as OLA, Single Base Extension, Invader and the like, assays for the detection of single nucleotide polymorphisms, sequencing, multiplex amplification including polymerase chain reactions, and the like.

Preferably, the assays are conducted in solution. Once the solution phase is performed, the experiments may include an array detection step. Arrays for detecting nucleic acids and nucleic acid reactions are more fully described in U.S. Ser. No. 09/556,463, filed Apr. 21, 2000, which is expressly incorporated herein by reference.

Pools of oligonucleotides find use in decoding arrays as described in more detail in U.S. Ser. No. 09/344,526, and U.S. Ser. No. 09/574,117, both of which are expressly incorporated herein by reference. In addition, pools of oligonucleotides find use in microfluidic systems as described in U.S. Ser. No. 09/306,369 which is expressly incorporated herein by reference. In addition, pools of oligonucleotides find use in composite array systems as described in U.S. Ser. No. 09/606,369, which is expressly incorporated herein by reference.

All references cited herein are incorporated by reference in their entirety.

We claim:

1. A method for multiplex detection of target nucleic acids comprising:
   a) providing a first substrate comprising greater than 50 different oligonucleotides linked to said first substrate through cleavable linkers, said greater than 50 different oligonucleotides having sequences different from each other, wherein said substrate comprises an array of discrete sites to which said greater than 50 different oligonucleotides are covalently linked;
   b) cleaving said linkers, thereby releasing said greater than 50 different oligonucleotides from said substrate thereby generating a pool of oligonucleotides comprising said greater than 50 different oligonucleotides;
   c) contacting said pool of oligonucleotides with a composition comprising different target nucleic acids, whereby said different target nucleic acids hybridize with said greater than 50 different oligonucleotides in said pool of oligonucleotides;
   d) modifying said greater than 50 different oligonucleotides in said pool of oligonucleotides hybridized with said different target nucleic acids to produce modified oligonucleotides, and
   e) contacting said modified oligonucleotides with a second substrate comprising probe oligonucleotides, said probe oligonucleotides having sequences different from each other and having sequences different from said greater than 50 different oligonucleotides released from said first substrate, whereby said target nucleic acids are detected.

2. A method for multiplex detection of target nucleic acids comprising:
   a) providing a first substrate comprising greater than 50 different oligonucleotides covalently linked to said first substrate through cleavable linkers, said greater than 50 different oligonucleotides having sequences different from each other, wherein said first substrate comprises an array of discrete sites to which said great than 50 different oligonucleotides are covalently linked;
   b) cleaving said linkers, thereby releasing said greater than 50 different oligonucleotides from said first substrate thereby generating a pool of oligonucleotides comprising said greater than 50 different oligonucleotides;
   c) contacting said pool of oligonucleotides with different target nucleic acids;
   d) modifying said greater than 50 different oligonucleotides in said pool of oligonucleotides contacted with said different target nucleic acids to produce modified oligonucleotides;
   e) contacting said modified oligonucleotides with a second substrate comprising probe oligonucleotides, said probe oligonucleotides having sequences different from each other and having sequences different from said pool of oligonucleotides released from said substrate, and
   f) detecting said target nucleic acids.

3. A method for multiplex detection of target nucleic acids comprising:
   a) cleaving greater than 50 different oligonucleotides linked to a first substrate through at least a first cleavable linker from said first substrate, wherein said first substrate comprises an array of discrete sites to which said greater than 50 different oligonucleotides are covalently linked, thereby releasing said greater than 50 different oligonucleotides from said first substrate generating a pool of oligonucleotides, said greater than 50 different oligonucleotides having sequences different from each other;
   b) contacting said pool of oligonucleotides with different target nucleic acids;
   c) modifying said greater than 50 different oligonucleotides contacted with said different target nucleic acids to produce modified oligonucleotides, and
   d) contacting said modified oligonucleotides with a second substrate comprising probe oligonucleotides, said probe oligonucleotides having sequences different from each other and having sequences different from said greater than 50 different oligonucleotides cleaved from said first substrate, and d) detecting said target nucleic acids.

4. A method for multiplex detection of target nucleic acids comprising:
  a) providing a first substrate comprising greater than 50 different oligonucleotides linked to said first substrate through cleavable linkers, said greater than 50 different oligonucleotides having different sequences, wherein said first substrate comprises an array of discrete sites to which said greater than 50 different oligonucleotides are covalently linked;
  b) cleaving said linkers, thereby releasing said greater than 50 different oligonucleotides from said substrate thereby generating a pool of oligonucleotides comprising said greater than 50 different oligonucleotides;
  c) contacting said pool of oligonucleotides with a composition comprising different target nucleic acids, whereby said target nucleic acids hybridize with said greater than 50 different oligonucleotides in said pool of oligonucleotides;
  d) modifying said greater than 50 different oligonucleotides hybridized with said target nucleic acids to produce modified oligonucleotides; and
  e) contacting said modified oligonucleotides with a second substrate comprising probe oligonucleotides, said probe oligonucleotides having sequences being different from each other and having sequences different from said greater than 50 different oligonucleotides released from said first substrate, said probe oligonucleotides being distributed randomly on said second substrate, whereby said target nucleic acids are detected.

5. A method for multiplex detection of target nucleic acids comprising:
  a) providing a first substrate on which are disposed different beads having greater than 50 different oligonucleotides covalently linked to said different beads through cleavable linkers, said greater than 50 different oligonucleotides having sequences different from each other, wherein said first substrate comprises an array of discrete sites on which said beads are disposed;
  b) cleaving said linkers, thereby releasing said greater than 50 different oligonucleotides from said beads, thereby generating a pool of oligonucleotides comprising said greater than 50 different oligonucleotides;
  c) contacting said pool of oligonucleotides with different target nucleic acids;
  d) modifying said greater than 50 different oligonucleotides in said pool of oligonucleotides contacted with said different target nucleic acids to produce modified oligonucleotides;
  e) contacting said modified oligonucleotides with a second substrate comprising probe oligonucleotides, said probe oligonucleotides having sequences different from each other and having sequences different from said pool of oligonucleotides cleaved from said beads, and
  f) detecting said target nucleic acids.

6. A method according to any one of claims 1, 2, 3, 4, or 5, wherein said greater than 50 different oligonucleotides are labeled.

7. A method according to claim 6, wherein said greater than 50 different oligonucleotides bear different labels.

8. A method according to any one of claims 1, 2, 3, or 4, wherein said first substrate comprises discrete sites to which said greater than 50 different oligonucleotides are covalently linked.

9. The method according to claim 1, 2, 3, 4, or 5, wherein said greater than 50 different oligonucleotides are synthesized by a synthesis method selected from the group consisting of printing and photolithography.

10. The method according to claim 1, 2, 3, 4 or 5, wherein said first substrate is selected from the group consisting of glass, plastics, polysaccharides, nylon, nitrocellulose resins, silica, silicon, carbon, and metals.

11. The method according to claim 1, wherein said first and second substrates comprises a chip.

12. A method according to claim 1, 2, 3, 4 or 5, wherein said modifying step comprises sequencing or amplification.

13. A method according to claim 1, 2, 3, 4 or 5, wherein said modifying step comprises polymerase chain reaction (PCR).

14. The method according to any one of claims 1, 2, 3, or 4, wherein said first substrate comprises greater than 1000 different oligonucleotides.

15. The method of claim 5, wherein said different beads comprise greater than 1000 different oligonucleotides.

16. The method of claim any one of claims 1, 2, 3, 4, or 5, wherein said modifying step comprises ligase chain reaction (LCR).

17. The method of claim any one of claims 1, 2, 3, 4, or 5, wherein said modifying step comprises cycling probe technology (CPT).

18. The method of claim any one of claims 1, 2, 3, 4, or 5, wherein said modifying step comprises Invader.

19. The method of claim any one of claims 1, 2, 3, 4, or 5, wherein said modifying step comprises oligonucleotides ligation assay (OLA).

20. The method of claim any one of claims 1, 2, 3, 4, or 5, wherein said modifying step comprises single base extension (SBE).

21. The method of claim any one of claims 1, 2, 3, 4, or 5, wherein said modifying step comprises amplification.

22. The method of claim any one of claims 1, 2, 3, 4, or 5, wherein said modifying step comprises rolling circle amplification.

* * * * *